United States Patent [19]
Abrams et al.

[11] Patent Number: 5,694,920
[45] Date of Patent: Dec. 9, 1997

[54] INHALATION DEVICE

[76] Inventors: Andrew L. Abrams, 26 Imperial Ave., Westport, Conn. 06880; Anand Gumaste, 7 Ardsley Ct., Robbinsville, N.J. 08691

[21] Appl. No.: 788,921

[22] Filed: Jan. 24, 1997

Related U.S. Application Data

[63] Continuation-in-part of Ser. No. 599,508, Jan. 25, 1996.

[51] Int. Cl.$^6$ .................................................. A61M 16/00
[52] U.S. Cl. ........................ 128/200.16; 128/203.12; 128/203.15; 128/203.21; 604/58
[58] Field of Search ................... 128/203.16, 203.12, 128/203.22, 200.23, 203.15, 203.21, 203.23, 204.21, 204.22; 604/58

[56] References Cited

U.S. PATENT DOCUMENTS

| | | | |
|---|---|---|---|
| 3,948,264 | 4/1976 | Wilke et al. | 128/203.15 |
| 5,619,984 | 4/1997 | Hodlon et al. | 128/203.15 |
| 5,655,523 | 8/1997 | Hodlon et al. | 128/203.15 |
| 5,673,686 | 10/1997 | Villax et al. | 128/203.15 |

FOREIGN PATENT DOCUMENTS

| | | | |
|---|---|---|---|
| 90/13328 | 11/1990 | WIPO | 128/203.15 |
| 92/07600 | 5/1992 | WIPO | 128/203.12 |

*Primary Examiner*—Vincent Millin
*Assistant Examiner*—V. Srivastava
*Attorney, Agent, or Firm*—Hayes, Soloway, Hennessey, Grossman & Hage, P.C.

[57] ABSTRACT

An inhaler includes a vibrator to deaggregated medication in powder form. One embodiment of the inhaler includes a piezoelectric vibrator 54 for vibrating a diaphragm for imparting vibration to a powder, and a controller 70 for controlling vibration so as to optimally suspend at least a portion of said powder in a fluidized state. An electrostatic charge plate 32 draws powder of selected particle size into the inhalation stream.

16 Claims, 5 Drawing Sheets

INHALATION DEVICE

This application is a continuation-in-part of co-pending application Ser. No. 08/599,508, filed Jan. 25, 1996, still pending.

BACKGROUND OF THE INVENTION

1. Field of the Invention

The present invention relates generally to the field of inhalation devices, and more specifically, to inhalation devices that utilize vibration to facilitate suspension of powder (e.g., powdered medication) into an inhaled gas stream (e.g., of inhaled air). Particular utility for the present invention is found in the area of facilitating inhalation of powdered medications (e.g., bacterial vaccines, sinusitis vaccines, antihistaminic agents, vaso-constricting agents, anti-bacterial agents, anti-asthmatic agents, theophylline, aminophylline, di-sodium cromolyn, etc.), although other utilities are contemplated, including other medicament applications.

2. Brief Description of the Prior Art

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. Alternatively, the drug in this form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drug is optimum when the drug particles delivered to the respiratory tract are between 1 to 5 microns in size. When the drug particles need to be in this size range the dry powder delivery system needs to address a number of issues:

(1) Small size particles develop an electrostatic charge on themselves during manufacturing and storage. This causes the particles to agglomerate or aggregate, resulting in clusters of particles which have an effective size greater than 5 microns. The probability of these large clusters making it to the deep lungs then decreases. This would result in a lower percentage of the packaged drug being available to the patient for absorption.

(2) The amount of active drug that needs to be delivered to the patient may be of the order of 10s of micrograms. For example, albuterol, in the case of a drug used in asthma, this is usually 25 to 50 micrograms. Current manufacturing equipment can effectively fill milligrams of drug with acceptable accuracy. So the standard practice is to mix the active drug with a filler or bulking agent such as lactose. This additive also makes the drug "easy to flow". This filler is also called a carrier since the drug particles also stick to these particles through electrostatic or chemical bonds. These carrier particles are very much larger than the drug particles in size. The ability of the dry powder inhaler to separate drug from the carrier is an important performance parameter in the effectiveness of the design.

(3) Active drug particles with sizes greater than 5 microns will be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bio-availability of the drug.

Prior art dry powder inhalers (DPIs) usually have a means for introducing the drug (active drug plus carrier) into a high velocity air stream. The high velocity air-stream is used as the primary mechanism for breaking up the cluster of micronized particles or separating the drug particles from the carrier. Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. No. 5,458,135.

These prior art devices present several problems and possess several disadvantages which are remedied by the inhalation devices of the present invention. For instance, these prior art devices require that the user exert considerable effort in inhalation to effect dispensing or withdrawal of powder from a pierced capsule into the inhaled air stream. With these prior art devices, suction of powder through the pierced holes in the capsule caused by inhalation generally does not withdraw all or even most of the powder out of the capsule, thus causing a waste of the medicament. Also, such prior art devices result in uncontrolled amounts or clumps of powdered material being inhaled into the user's mouth, rather than a constant inhalation of controlled amounts of finely dispersed powder.

The above description of the prior art is taken largely from U.S. Pat. No. 3,948,264 to Wilke et at, who disclose a device for facilitating inhalation of a powdered medication that includes a body portion having primary and secondary air inlet channels and an outlet channel. The secondary inlet channel provides an enclosure for a capsule containing the powdered medication and the outlet channel is formed as a mouthpiece protruding from the body. A capsule piercing structure is provided, which upon rotation puts one or more holes in the capsule so that upon vibration of the capsule by an electro-mechanical vibrator, the powdered drug may be released from the capsule. The piercing means disclosed in Wilke et al includes three radially mounted, spring-biased piercing needles mounted in a trochoidal chamber. Upon hand rotation of the chamber, simultaneous inward radial motion of the needles pierces the capsule. Further rotation of the chamber allows the needles to be retracted by their spring mountings to their original positions to withdraw the needles from the capsule. The electromechanical vibrator includes, at its innermost end, a vibrating plunger rod which projects into the intersection of the inlet channel and the outlet channel. Connected to the plunger rod is a mechanical solenoid buzzer for energizing the rod to vibrate. The buzzer is powered by a high energy electric cell and is activated by an external button switch. According to Wilke et al, upon inhalation through outlet channel 3 and concurrent pressing of switch 10d to activate the electromechanical vibrating means 10, air is sucked through inlet channels 4 and 12 and the air stream through the secondary inlet channel 4 raises the capsule up against the vibrating plunger rod 10a. The capsule is thus vibrated rapidly with powder being fluidized and dispensed from the pierced holes therein. (This technique is commonly used in manufacturing for dispensing powder through a hopper where the hopper is vibrated to fluidize the powder and move it through the hopper outlet. The pierced holes in the capsule represent the hopper outlet.) The air stream through inlet channel 4 and 12 aids in withdrawal of powder from the capsule and carries this powder through the outlet channel 3 to the mouth of the user." (Wilke et at, column 3, lines 45–55). Wilke et al further discloses that the electromechanical vibrator means may be placed at a right angle to the inlet chamber and that the amplitude and frequency of vibration may be altered to regulate dispensing characteristics of the inhaler.

Thus, as noted above, the vibrator in Wilke et al's disclosed inhaler is an electromechanical device consisting of a rod driven by a solenoid buzzer. (This electromechanical means may be a motor driving a cam [Col. 4, Line 40]). A disadvantage of the inhaler implementation as disclosed by Wilke is the relatively large mechanical movement required of the rod to effectively vibrate the capsule. The large movement of the rod, usually around 100s of microns, is necessary due to the elasticity of the capsule walls and inertia of the drug and capsule.

Moreover, solenoid buzzers typically have operating frequencies less than 5 Khz. This operating frequency tends to be noisy and therefore is not desirable when incorporated into a dry powder inhaler from a patient's perspective. A further disadvantage of the electrochemical actuators of Wilke is the requirement for a high energy source (Wilke et al, Col. 3, line 38), thus requiting a large battery source or frequent changes of the battery pack for portable units. Both these features are not desirable from a patient safety and "ease of use" standpoint.

The inhaler of Wilke et al is primarily intended to reduce the amount of powder left behind in the capsule relative to other inhalers cited in the patent disclosure. (Wilke et at, Col. 4, lines 59–68, Col. 5, lines 1–48). However, Wilke et al does not address the need to deaggragate the powder into particle sizes or groups less than 6 microns in size as is required for effective delivery of the medication to the lungs; rather Wilke et at, like the prior art inhalers continues to rely on the air stream velocity to deaggregate the powder ejected into the air stream, into particle sizes suitable for delivery to the lungs.

Another prior art inhalation device is disclosed in Bums et al U.S. Pat. No. 5,284,133. In this device, a liquid medication is atomized by an ultrasonic device such as a piezo element (Bums et at, Col. 10, lines 36–51). A stream of air, usually at a high velocity, or a propellant then carries the atomized particles to the patient. The energy required to atomize the liquid medication in the nebulizer is prohibitively high, making this approach for the delivery of drugs to the lungs only feasible as a desk top unit. The high voltage requirements to drive the piezo, to produce the necessary mechanical displacements, also severely effects the weight and size of the device. It is also not obvious that the nebulizer operating principles can be applied to the dry powder inhalers for delivery or powder medication to the lungs.

The prior art devices therefore have a number of disadvantages which makes them less than desirable for the delivery of dry powder to the lungs. Some of these disadvantages are:

The performance of the prior art inhalers depends on the flowrate generated by the user. Lower flowrate does not result in the powder being totally deaggregated and hence adversely affects the dose delivered to the patient.

Inconsistency in the bioavailability of the drugs from dose-to-dose because of lack of consistency in the deaggregation process.

Large energy requirements for driving the electromechanical based inhalers which increases the size of the devices making them unsuitable for portable use.

SUMMARY OF THE INVENTION

Thus, it is the general object of the invention to provide an inhaler that is capable of deaggregating and separating the particles by size and further suspending them in the air stream, independent of air stream velocity. Accordingly, one embodiment of the inhaler of the present invention includes a piezoelectric vibrator for vibrating the drag, which may be a pure micronized drag or a micronized drug on a carrier, in a container such as a blister pack so as to deaggregate clumps of the drug or separate the micronized drug from the carrier particles. Since the intent of the invention is to ensure consistency in the bioavailability of the drug from dose-to-dose, the amount of energy coupled into the powder is sufficient to cause deaggregation to happen and maintain the powder in a fluidized state, but is not so high as to prematurely eject clumps of powder into the air stream that is flowing across the blister. The micronized particle sizes of interest are then lifted out of this fluidized powder by an electrostatic field that is established across the air stream. By controlling the strength of the electrostatic field only particle sizes of interest are introduced into the air stream. The larger size particles are left behind in the container. This reduces the inconsistency associated with the bioavailability of the drag because of the large particles being deposited into the mouth or throat as is common with devices described in prior art.

In a second embodiment, a vibrator having a vibrating diaphragm is provided for imparting vibrations to the powder. The vibrator may include electrostatic, electromagnetic, or magnetostrictive means for rapidly deflecting the diaphragm. The magnetostrictive means uses at least one ferromagnetic member adapted to change its dimensions and/or shape in the presence and as a function of the magnetic flux applied to the member by a magnetic flux generating means. The magnetic flux generating means may comprise a permanent magnet and a coil, or an electromagnetic means for generating and applying the magnetic flux to the ferromagnetic member.

BRIEF DESCRIPTION OF THE DRAWINGS

Reference is made to the drawings, wherein like numerals depict like parts, and wherein:

FIG. 1A and B are side elevations of the inhaler of the present invention;

FIG. 2 is an end view of the embodiment of FIG. 1;

DETAILED DESCRIPTION OF PREFERRED EMBODIMENT

Figure 1A:
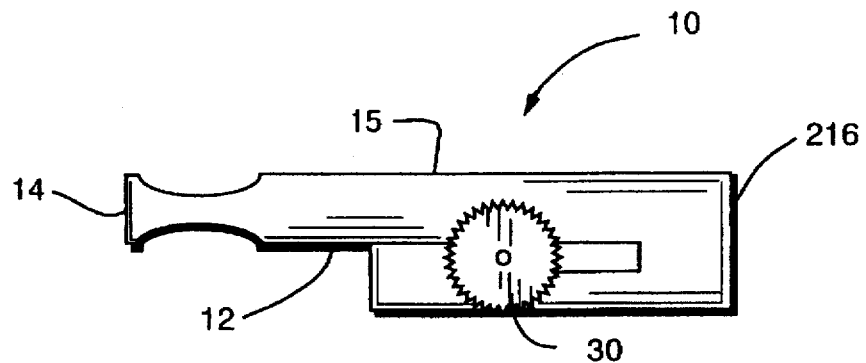
Figure 1B:
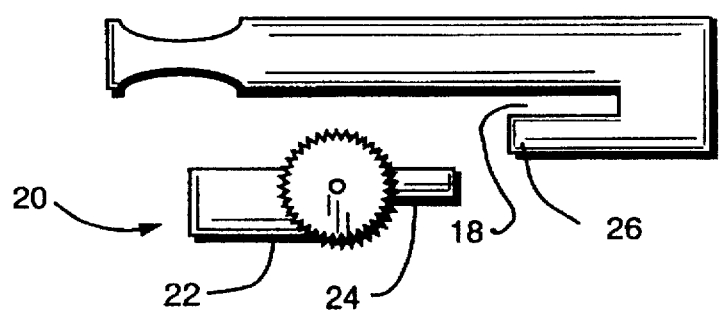
Figure 2:
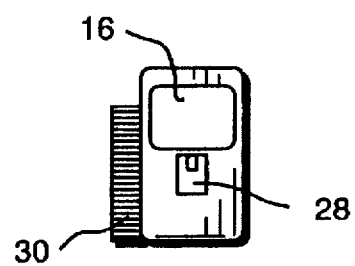
Figure 3A:
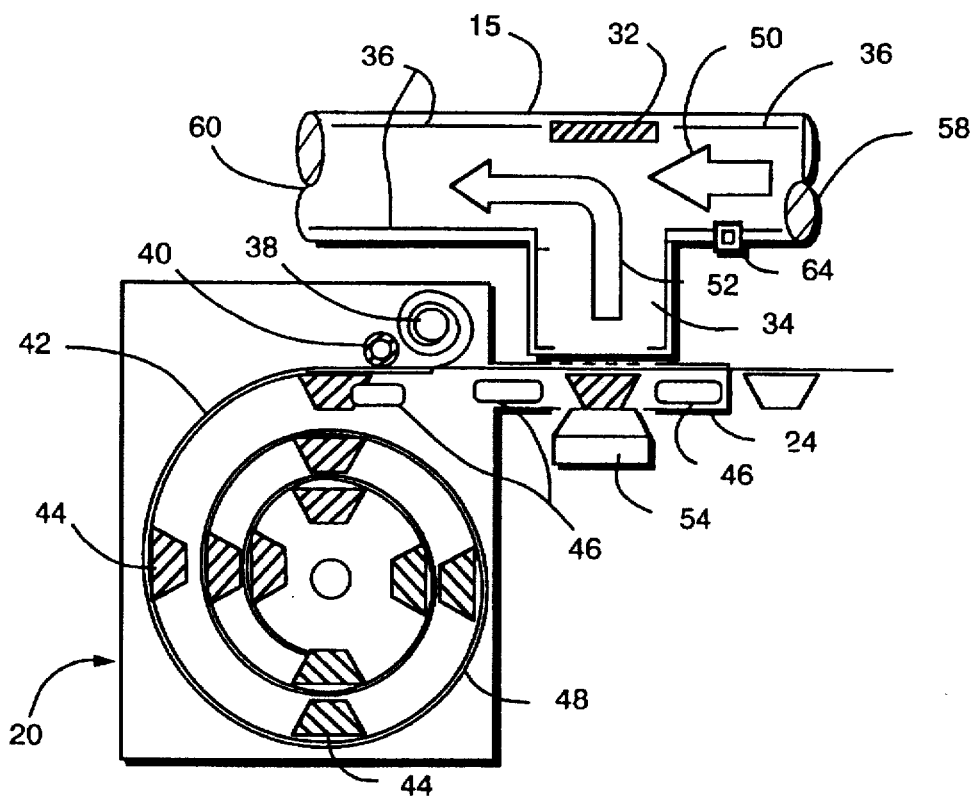
FIGS. 3A and 3B is an enlarged cross-sectional views of the embodiment of FIG. 1.
Figure 3B:
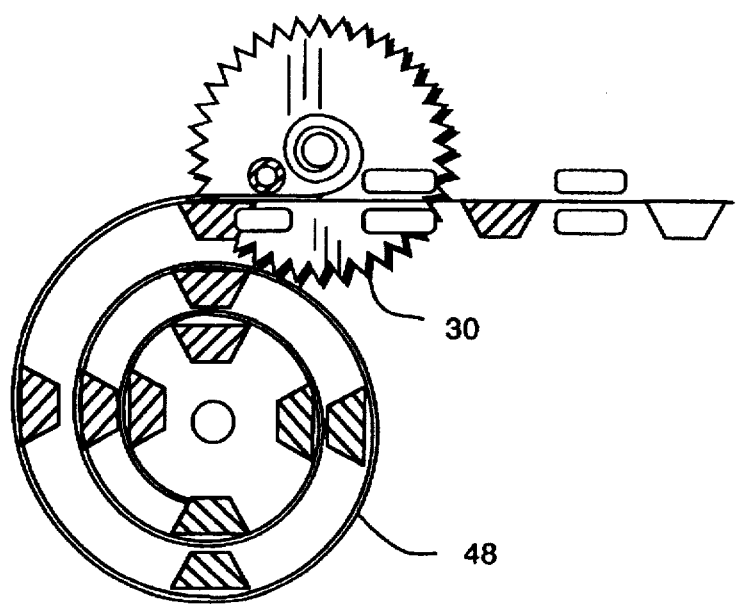
Figure 4:
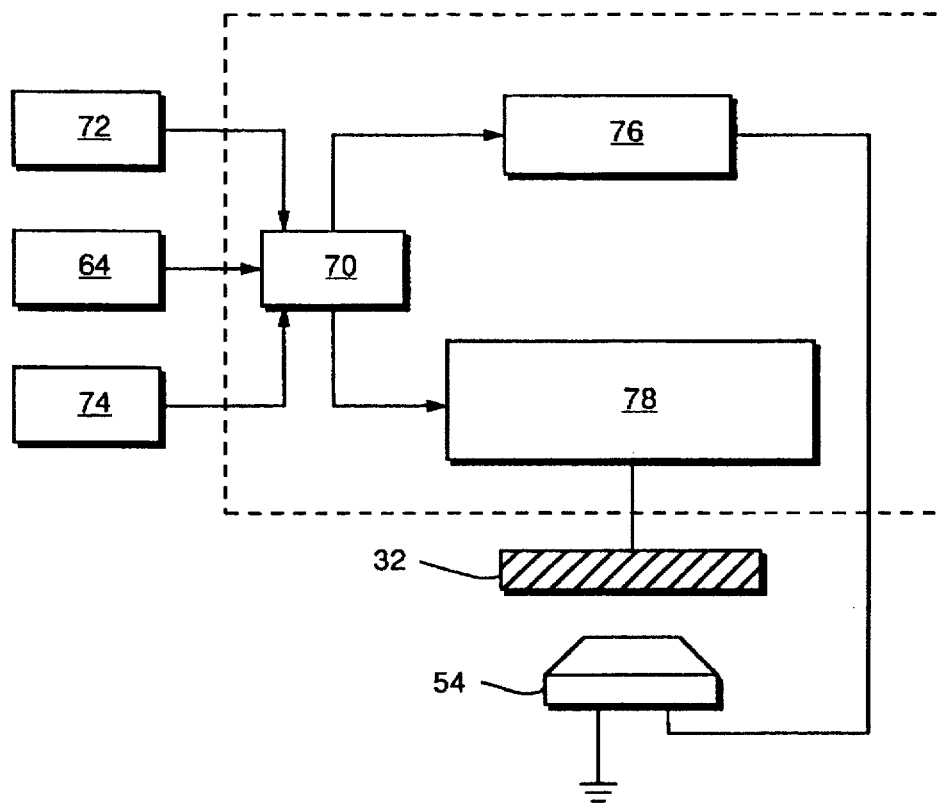
FIG. 4 is a functional schematic diagram of the electrical/electronic system used in the inhaler of FIG. 1.
Figure 5:
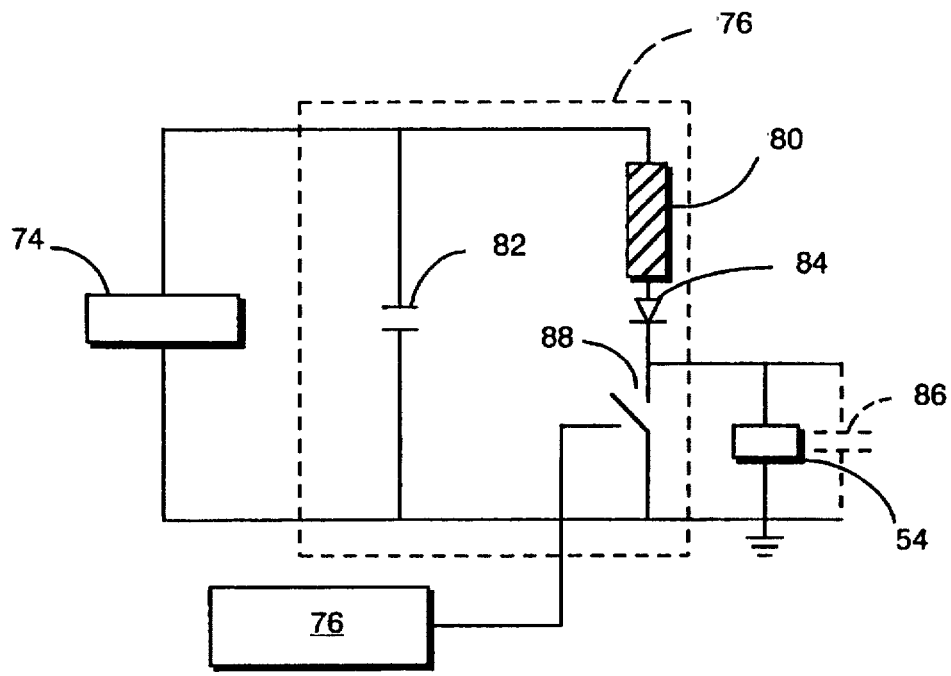
FIG. 5 is a schematic representation of the preferred vibrator driver circuit used for exciting the piezoelectric vibrator.

Referring to FIGS. 1–6, one preferred embodiment 10 of the inhaler of the present invention will now be described. The inhaler 10 comprises a housing 12 having a mouthpiece 14 at one end of leg 15 thereof, and an air inlet opening 16 at the opposite end of the same leg 15. The leg 15 forms a hollow channel that is unobstructed between the opening 14 and 16. Referring in particular to FIG. 3, a passageway 34 is formed in leg 15 intermediate of mouthpiece 14 and inlet 16. This passageway communicates with a drug cartridge 20. Opposite this passageway 34 is a high frequency piezoelectric 54 vibrator located in member 26 of the inhaler housing 12. An inhalation sensor 64 is also located between the passageway 34 and the inlet 16 of the inhaler.

Disposable cartridge 20 comprises an outer housing 22 which includes a tab 24 for slidably mounting in recess 18 formed integrally to the housing 12. Drug cartridge 20 includes a coiled tape 48 carrying a plurality of spaced blisters or wells 44 for carrying a dry powder medicament. A release film 42 covers and seals wells 44. Tape 48 is formed as a coil, and threaded between guide platen 46 and pinch roller 40. Pinch roller 40 is driven by a take-up spool 38 which in mm is driven by the thumbwheel 30. In use, as the thumbwheel 30 is turned, it peels the release film 42 from the tape 48 to expose the wells 44 carrying the drug, and the release film is collected by the take-up spool 38. This collection of the release film advances a new well carrying the drug over the piezoelectric vibrator 54 housed in location 26 of the inhaler housing 15. Tape 48 also preferably includes detent means or the like for indexing the tape so a selected well 44 is automatically positioned over the piezoelectric element 54.

Referring to FIG. 3A, a passageway 34 allows the selected well 44 to communicate with the hollow channel 15. Passageway 34 should be of sufficient length to serve the purpose of avoiding to introduce the drug prematurely into the air stream 50, which could be zero, if the wells 44 have sufficient depth. Above the exposed well 44, in the passageway 34, is an electrostatic plate 32 on the inside wall of the hollow channel 15. Channel 15 also includes an inhalation sensor 64, the purpose of which is to detect the flow of an air stream from the inlet 16 to the mouthpiece 14. This sensor signal is used to sequence the electronic control of the inhaler to ensure repeatable performance.

A brief description of the sequence of operation is as follows. A new well 44 carrying the drug is advanced forward and positioned over the piezoelectric element 54. A power switch 72 on the inhaler housing 12 (not shown in figure) is turned on. This connects the power source 74 to the electronics. At this point the output of the actuation controller circuit 70 is not enabled. When a minimum air-stream 50 flowrate is established, the actuation controller 70 enables the vibrator driver circuit 76 and the electrostatic voltage generator circuit 78. The high frequency vibrations set up by the piezoelectric vibrator 54 are coupled through the well 44 into the powder. These high frequency vibrations deaggregate the powder in the well and keep the powder in a fluidized state. The electrostatic plate 32 sets up an electrostatic field across the fluidized powder. The deaggregated particles, which carry an electrostatic charge, experience an electrostatic force and are lifted up by this field set up by the electrostatic plate 32. This electrostatic force experienced by the charged particles is counteracted by the mass of the particles. Smaller particles which are unable to counteract their mass are lifted up toward the electrostatic plate 32, while larger size particles which cannot counteract their mass are left behind in the well 44. The voltage applied to the electrostatic plate 32 is selected so that only deaggregated drug particles, i.e. smaller size particles of choice, are lifted towards the electrostatic plate 32, where enter the air stream 50 and are carried to the mouthpiece 14. On the other hand, the electrostatic force on the charged particles is not so strong as to enable the particles to make it across the air stream 50 to the electrostatic plate 32.

The inner surface of the channel 15 and the passageway 34 is metalized and connected to ground. Without this metalization 36, static charges could build up on the inside surfaces of the channel 15 and passageway 34, and attract charged drag particles as they are lifted out of the well 44 and make their way to the mouthpiece 14, thus reducing reproducibility of delivery from dose-to-dose of the inhaler.

FIG. 5 shows a preferred schematic embodiment of the vibrator drive circuit 76. This configuration helps couple energy efficiency to the high frequency piezoelectric vibrator 54, while at the same time generating the necessary high voltages for driving the piezo. This circuit configuration enables the inhaler to be designed as a portable unit and enables it to achieve very small package dimensions relative to similar units described in the prior art. The circuit consists of an inductance 80 in series with a diode 84 and switch 88. The switch 88 may be of a bipolar transistor or a field effect transistor or any other means capable of switching at high frequency in an efficient manner, i.e. without loss of considerable energy. Elements 80, 84 and 88 are connected across a bypass capacitor 82 capable of carrying high frequency currents. The piezoelectric element 54 is connected across switch 88. The actuation controller 70 switches the switch 88 on and off at the appropriate frequency necessary to drive the piezoelectric vibrator. The sequence of operation is as follows: When switch 88 is turned ON, current builds up in the inductance 80. When switch 88 is turned OFF, the inductance 80 then resonates with the internal capacitor of the piezo element 54. This series resonant circuit efficiently couples the energy stored in the inductance to the piezo element while at the same time generating the high voltage necessary to drive it. If necessary, the internal capacitance of the piezo may be supplemented by an external capacitor 86 to control the energy/voltage transfer characteristics to the piezo 54.

FIGS. 6A and 6B show the schematic representation of the electrostatic voltage generation circuit 78. The FIG. 6A schematic is suitable for generating low voltages, for example, less than 200 volts. The actuation controller 70 turns a switch 96 ON and OFF at a frequency which will result in efficient build up of voltage across capacitor 94. When switch 96 turns ON, current builds up in an inductance coil 90. When switch 96 is mined OFF, the inductance pumps this energy into the output capacitor 94 by generating a voltage one diode drop higher than the output voltage. The inductor 90 continues to maintain this voltage till all the energy stored in it is transferred to capacitor 94. The electrostatic plate 32 is connected to capacitor 94. The voltage generated across capacitor 94 sets up the electrostatic field across the fluidized and deaggregated powder in the well 44. Capacitor 95 is a bypass capacitor for carrying the high frequency switching currents.

Figure 6A:
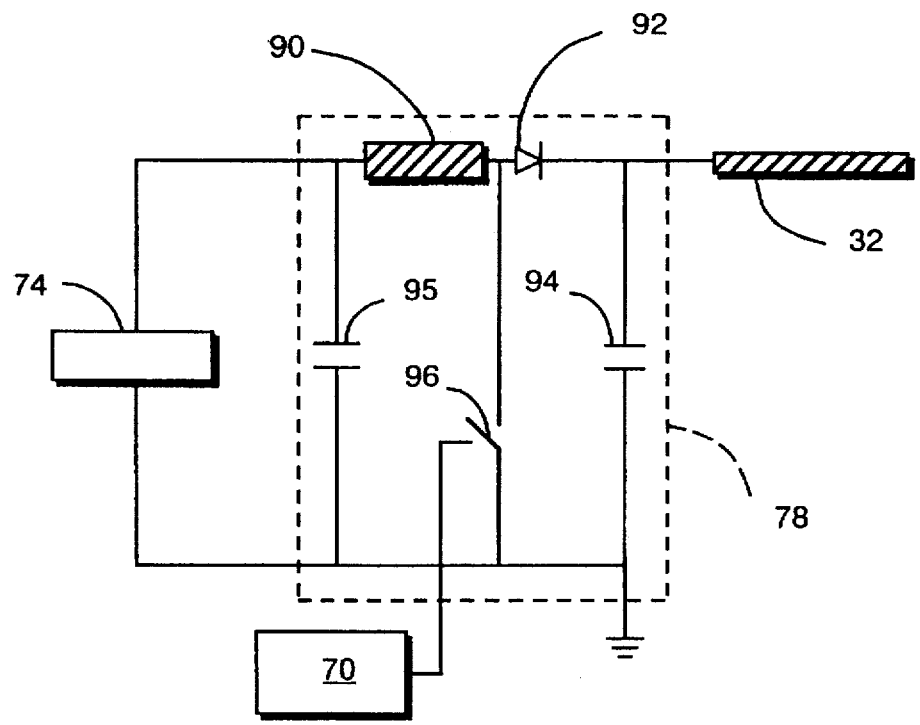
FIGS. 6A and 6B are schematic representations of the electrostatic voltage generation circuit used in the inhaler of FIG. 1.
Figure 6B:
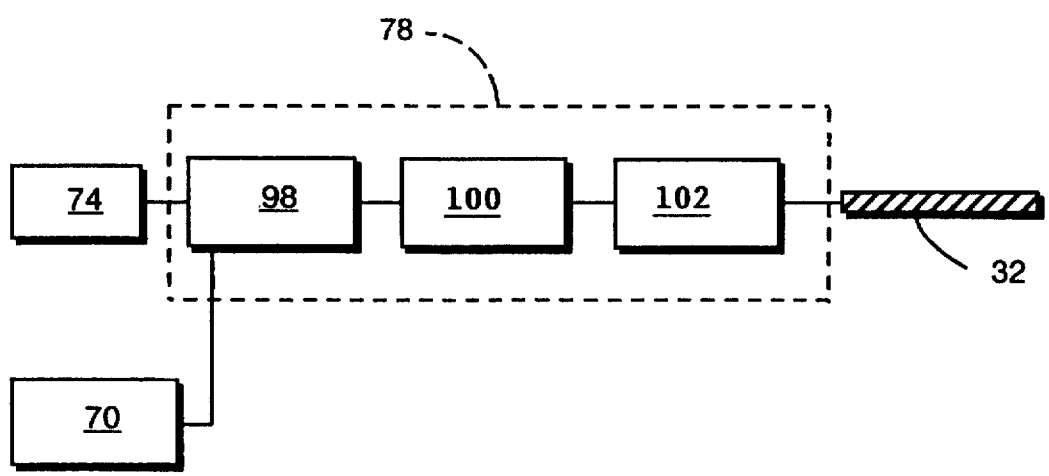

If a higher electrostatic field is required, it may be necessary to use the schematic shown in FIG. 6B. Here a high frequency inverter 98 is coupled to a high frequency transformer 100. The output of transformer 100 feeds into a voltage multiplier circuit 102 for stepping up the voltage to the required level. The output of the voltage multiplier circuit is connected to the electrostatic plate.

Figure 7:
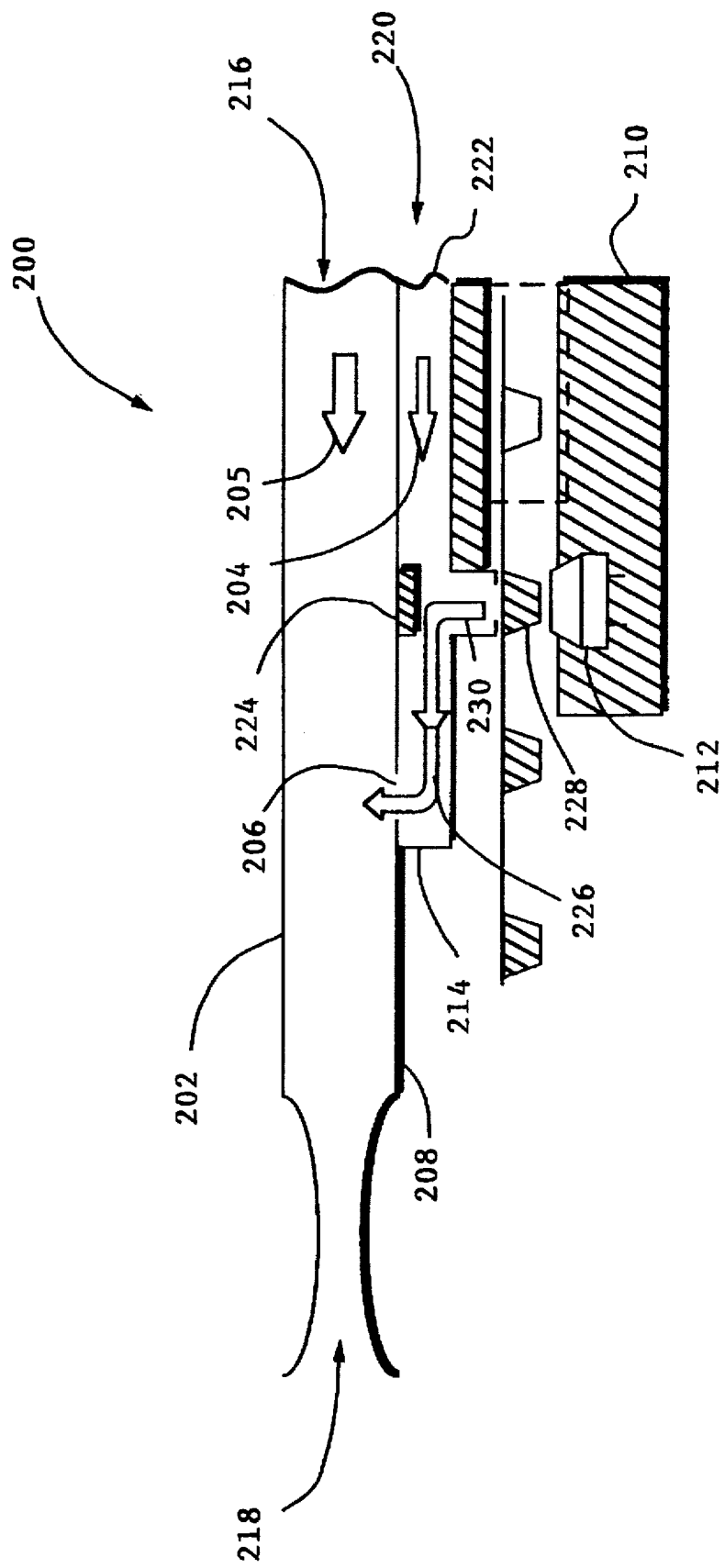
FIG. 7 is a view similar to FIG. 3A, and showing an alternative embodiment of the present invention.

FIG. 7 shows yet another embodiment 200 of the present invention. This embodiment would be suitable for those applications where we wish to further reduce the possibility of air turbulence picking up the partially deaggregated powder from the blister wells. This embodiment consists of a housing 202 which includes a mouthpiece 218 at one end of a main leg 208, and a main air inlet 216 at the opposite end of the leg 208. An opening 206 is provided at one end of a secondary leg 214 that opens into the main leg 208, and an air inlet 220 is provided at the opposite end of the secondary leg 214. Housing 202 also includes a high frequency vibrator, such as piezoelectric vibrator 212, located in member 210 of the housing 202. A secondary channel 230 communicates with the secondary leg 214 at one end and a drug container 228 at the other end. Channel 230 allows the selected drug container to communicate with the secondary leg 214. Directly under the drug container is the vibrator 212.

The FIG. 7 embodiment operates as follows: A new well 228 carrying the drug is advanced forward and positioned over the piezoelectric vibrator 212. A power switch 72 on the inhaler housing (not shown in the figure) is turned on. This connects the power to the electronics. When the patient inhales a main air flow 205 and a secondary air flow 204 is established. The secondary air flow 204 causes a flapper valve 222 to open and enables the vibrator drive circuit 76 and the electrostatic generator circuit 78. The flapper valve functions as an air flow sensor. The high frequency vibrator 212 deaggregates the powder in the container 228 and keeps it in a fluidized state. An electrostatic plate 224 sets up an electrostatic field across the fluidized powder. The deaggregated particles which carry a charge are lifted up towards electrostatic plate 224. The resulting particle stream 226 is introduced into the air stream 204 and is carried forward and introduced into the main air stream 205.

It will be appreciated that although the foregoing detailed description proceeded with reference being made to the preferred embodiments and methods of use, the present invention is not intended to be limited to these preferred embodiments and methods of use. Rather, the present invention is of broad scope and is intended to be limited only as set forth in the accompanying claims.

What is claimed is:

1. An inhalation device, for dispensing of medication in a powder form, having a body comprising an air outlet channel in said body portion providing a mouthpiece for inhalation of air by the user;

a primary air inlet channel in said body portion communicating with said air outlet channel;

a secondary channel in said body portion communicating at one end thereof with said primary air inlet channel and said air outlet channel forming an air stream, and at its other end with supply of said medication in powder form, a high frequency vibrator for deaggregating the powder in said secondary channel, and an electrostatic means to separate by size the deaggregated powder in said channel and introduce the powder particles of size interest into the air stream.

2. An inhalation device according to claim 1, wherein the high frequency vibrator comprises a piezoelectric vibrator.

3. An inhalation device according to claim 1, wherein the high frequency vibrator comprises a magnetostrictive type inhaler.

4. An inhalation device according to claim 1, wherein the high frequency vibrator comprises an electrostatic condenser driven diaphragm.

5. An inhalation device according to claim 2, and comprising a series resonant circuit for transferring energy to the piezoelectric vibrator.

6. An inhalation device according to claim 1, and comprising a charge-pump circuit for generating an electrostatic voltage for driving said high frequency generator.

7. An inhalation device according to claim 1, and comprising a high frequency inverter, a high frequency transformer and a voltage multiplier circuit for generating an electrostatic voltage for driving said high frequency generator.

8. An inhalation device according to claim 1, and further comprising an inhalation sensor for activating said high frequency vibrator in response to inhalation of air by the user.

9. An inhaler device according to claim 1, wherein the inside surfaces of said air channels are metalized and connected to electrical ground.

10. An inhalation device, for dispensing of medication in a powder form, having a body comprising an air outlet channel in said body portion providing a mouthpiece for inhalation of air by the user;

a primary air inlet channel in said body portion communicating with said air outlet channel;

a secondary air inlet channel in said body portion communicating with said air outlet channel;

a secondary channel in said body portion communicating at one end thereof with said secondary air inlet channel and said air outlet channel forming a secondary air stream, and at its other end with a supply of said medication in powder form, a high frequency vibrator for deaggregating the powder, and an electrostatic means to separate by size the deaggregated powder and introduce the powder particles of size interest into said secondary air stream.

11. An inhalation device according to claim 10, wherein the high frequency vibrator comprises a piezoelectric vibrator.

12. An inhalation device according to claim 10, wherein the high frequency vibrator comprises a magnetostrictive type vibrator.

13. An inhalation device according to claim 10, wherein the high frequency vibrator comprises an electrostatic condenser driven diaphragm.

14. An inhalation device according to claim 11, and comprising a series resonant circuit for transferring energy to the piezoelectric vibrator.

15. An inhalation device according to claim 10, and comprising a charge-pump circuit for generating the electrostatic voltage for driving said high frequency generator.

16. An inhalation device according to claim 10, and comprising a high frequency inverter, a high frequency transformer and a voltage multiplier circuit for generating the electrostatic voltage for driving said high voltage vibrator.

* * * * *